(12) United States Patent
Kosel et al.

(10) Patent No.: US 11,078,453 B2
(45) Date of Patent: Aug. 3, 2021

(54) NANONEEDLES FOR INTRACELLULAR APPLICATIONS

(71) Applicant: KING ABDULLAH UNIVERSITY OF SCIENCE AND TECHNOLOGY, Thuwal (SA)

(72) Inventors: Jürgen Kosel, Thuwal (SA); Mincho Nikolaev Kavaldzhiev, Thuwal (SA); Jose Efrain Perez, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 336 days.

(21) Appl. No.: 16/066,724

(22) PCT Filed: Jan. 3, 2017

(86) PCT No.: PCT/IB2017/050013
§ 371 (c)(1),
(2) Date: Jun. 28, 2018

(87) PCT Pub. No.: WO2017/118921
PCT Pub. Date: Jul. 13, 2017

(65) Prior Publication Data
US 2018/0355297 A1    Dec. 13, 2018

Related U.S. Application Data

(60) Provisional application No. 62/274,492, filed on Jan. 4, 2016.

(51) Int. Cl.
*C12M 1/26*    (2006.01)
*B81B 1/00*    (2006.01)
(Continued)

(52) U.S. Cl.
CPC ............... *C12M 1/26* (2013.01); *A61B 5/685* (2013.01); *A61B 10/0045* (2013.01);
(Continued)

(58) Field of Classification Search
None
See application file for complete search history.

(56) References Cited

U.S. PATENT DOCUMENTS 6,334,856 B1 *  1/2002  Allen ................. A61B 5/14514
                                                      604/191
7,344,499 B1 *  3/2008  Prausnitz .......... A61M 37/0015
                                                      600/309

(Continued)

FOREIGN PATENT DOCUMENTS

CN    101623535 A  *  1/2010  ........ A61M 37/0015
EP    2671613 A2      12/2013

OTHER PUBLICATIONS

Milan et al ; Fundamentals of Electrochemical Deposition; Second Edition; 2006; pp. 169-175. (Year: 2006).*

(Continued)

*Primary Examiner* — Shamim Ahmed
(74) *Attorney, Agent, or Firm* — Patent Portfolio Builders PLLC

(57) ABSTRACT

Nanoneedles and nanoneedle arrays and methods of making nanoneedles are provided. The methods can include multi-layer fabrication methods using a negative photoresist and/or a positive photoresist. The nanoneedle arrays include one or more nanoneedles attached to a surface of a substrate. The nanoneedle can have both a proximal opening and a distal opening, and an inner passageway connecting the proximal opening and the distal opening. The nanoneedle can have a functional coating. The nanoneedle can include iron, cobalt, nickel, gold, and oxides and alloys thereof. The nanoneedle arrays can be used for the administration and/or the extrac- (Continued)

tion of agents from individual cells. In one or more aspects, the nanoneedles can be magnetic nanoneedles. An oscillating magnetic field applied to a magnetic nanoneedle can induce one or both of heating and vibration of the magnetic nanoneedle. The heating and/or vibration can cause a magnetic nanoneedle to penetrate the wall of a cell.

8 Claims, 6 Drawing Sheets

(51) Int. Cl.
    *A61B 10/02*     (2006.01)
    *A61B 5/00*     (2006.01)
    *A61B 10/00*     (2006.01)
    *B81C 1/00*     (2006.01)
    *A61M 37/00*     (2006.01)
    *C12M 1/00*     (2006.01)
    *B82Y 5/00*     (2011.01)

(52) U.S. Cl.
    CPC ..... *A61B 10/0233* (2013.01); *A61M 37/0015* (2013.01); *B81B 1/008* (2013.01); *B81C 1/00111* (2013.01); *C12M 23/20* (2013.01); *A61B 2010/0225* (2013.01); *A61M 2037/003* (2013.01); *A61M 2037/0023* (2013.01); *A61M 2037/0053* (2013.01); *B81B 2201/055* (2013.01); *B82Y 5/00* (2013.01)

(56) References Cited

U.S. PATENT DOCUMENTS

| | | |
|---|---|---|
| 2004/0063100 A1 | 4/2004 | Wang |
| 2006/0286490 A1* | 12/2006 | Sandhu ................ G03F 7/0002 430/394 |
| 2014/0106262 A1* | 4/2014 | Tu ............................ G03F 1/46 430/5 |
| 2014/0256078 A1* | 9/2014 | Jin .......................... B28D 5/00 438/57 |
| 2014/0295558 A1 | 10/2014 | Chen et al. |
| 2015/0343390 A1* | 12/2015 | Ansari ..................... C25D 3/12 210/500.25 |

OTHER PUBLICATIONS

International Search Report in related International Application No. PCT/IB2017/050013, dated May 31, 2017.
Matsumoto, D., et al., "Oscillating High-Aspect-Ratio Monolithic Silicon Nanoneedle Array Enables Efficient Delivery of Functional Bio-Macromolecules into Living Cells," Scientific Report, Oct. 16, 2015, vol. 5, pp. 15325-1533.
Peer, E., et al., "Hollow Nanoneedle Array and Its Utilization for Repeated Administration of Biomolecules to the Same Cells," ACS Nano, Jun. 26, 2012, vol. 6, No. 6, pp. 4940-4946.
Written Opinion of the International Searching Authority in related International Application No. PCT/IB2017/050013, dated May 31, 2017.
Yang, H.Y., et al., "Ultraviolet Laser Action in Ferromagnetic Zn1—xFex0 Nanoneedles," Nanoscale Research Letters, Nov. 1, 2009, vol. 5, No. 1., pp. 247-251.
Yang, Z., et al., "Molecular Extraction in Single Live Cells by Sneaking In and Out Magnetic Nanomaterials," Proceedings National Academy of Sciences PNAS, Jul. 16, 2014, vol. 111, No. 30, pp. 10966-10971.
Berthing, T., et al., "Cell Membrane Conformation at Vertical Nanowire Array Interface Revealed by Fluorescence Imaging," Nanotechnology, vol. 23, No. 41, Sep. 25, 2012, pp. 1-8.
Chen, X., et al., "A Diamond Nanoneedle Array for Potential High-Throughput Intracellular Delivery," Advanced Healthcare Materials, vol. 2, Issue 8, 2013 (Published Online Feb. 27, 2013), pp. 1103-1107.
Chou, L.Y.T., et al., "Strategies for the Intracellular Delivery of Nanoparticles," Chem. Soc. Rev., vol. 40, Issue 1, Jan. 1, 2011, pp. 233-245.
Shalek, A.K., et al., "Vertical Silicon Nanowires as a Universal Platform for Delivering Biomolecules into Living Cells," Proc. Natl. Acad. Sci. U.S.A., vol. 107, No. 5, Feb. 2, 2010, pp. 1870-1875.
Takahashi, K., et al., "Induction of Pluripotent Stem Cells from Adult Human Fibroblasts by Defined Factors," Cell, vol. 131, No. 5, Nov. 30, 2007 (Published Online Nov. 20, 2007), pp. 861-872.
Wang, Y., et al., "Poking Cells for Efficient Vector-Free Intracellular Delivery," Nature Communications, vol. 5:4466, Jul. 29, 2014, pp. 1-31, Available at: http://www.ncbi.nlm.nih.gov/pubmed/25072981.

* cited by examiner

NANONEEDLES FOR INTRACELLULAR APPLICATIONS

CROSS-REFERENCE TO RELATED APPLICATIONS

This application is a U.S. National Stage Application of International Application No. PCT/IB2017/050013, filed on Jan. 3, 2017, which claims priority to, and the benefit of, U.S. provisional application entitled "MAGNETIC NANONEEDLES FOR INTRACELLULAR APPLICATIONS" having Ser. No. 62/274,492, filed Jan. 4, 2016, the contents of which are incorporated by reference in their entirety.

TECHNICAL FIELD

The present disclosure generally relates to devices for delivering agents to and/or extracting agents from individual cells.

BACKGROUND

Accessing the cell cytoplasm through cell membrane deformation can allow for a plethora of molecules or materials to be delivered into living cells. Such delivery holds potential for many biological applications. For instance, the delivery of quantum dots or nanoparticles to the cell cytoplasm would allow studying intracellular dynamics and to test novel therapeutics (5). Similarly, the delivery of genes has proven helpful for reprogramming cells into a pluripotent state, paving the way for cell-based therapy (6).

In a similar fashion, many different molecules, such as DNA, RNA, peptides and proteins, depend on intracellular delivery for them to be functional. Cells have been grown on nano needle substrates before, and it was found that there are difficulties for needles to penetrate the cells (1). Rather, the cell membrane indents dramatically over the needle.

There remains a need for improved systems and methods for delivering agents to cells.

Additionally, there remains a need for improved systems and methods for extracting agents from cells.

It is therefore an object of this disclosure to provide improved systems and methods for overcoming these deficiencies.

SUMMARY

The present disclosure provides nanoneedles and nanoneedle array devices and methods of making nanoneedles and nanoneedle array devices. The nanoneedles can be remotely operated. In an embodiment, the methods include multilayer fabrication using a positive photoresist and/or a negative photoresist or 3D printing with negative resist. The nanoneedle arrays can be used for the delivery of agents to cells and/or the extraction of agents from cells without killing the cells or without a significant impact of the cellular viability.

In one or more aspects, a nanoneedle array is provided having a substrate with an upper surface, and a nanoneedle attached to the upper surface. The nanoneedle can include both a proximal opening and a distal opening, and an inner passageway connecting the proximal opening and the distal opening. The nanoneedle can include a coating layer for delivering agents.

In one or more aspects the nanoneedle can be grown on a biocompatible substrate such as a silicon substrate or a glass substrate. In some aspects the nanoneedles contain a material selected from the group consisting of iron, cobalt, nickel, gold, and oxides and alloys thereof.

The nanoneedles can have a variety of dimensions including widths of about 100 nm to 1000 nm. In various aspects the nanoneedles can have aspect ratios of about 1 to 20.

Methods of fabrication of the nanoneedles on a surface of a substrate using a negative photoresist are provided. The methods can include depositing a thin-film of a conductive metal layer onto an upper surface of a substrate. In some aspects, the methods can include patterning a negative photoresist layer onto the conductive metal layer. In some aspects the methods can include electroplating a material onto the conductive metal layer using the patterned negative photoresist layer to form the nanoneedle having an inner passageway. In one or more aspects, the material on the conductive metal layer can be selected from the group consisting of iron, cobalt, nickel, gold, and oxides and alloys thereof. In some aspects, the material on the conductive metal layer can be a metal, including a transition metal such as iron, cobalt, nickel, or an oxide or alloy thereof. In certain aspects etching of the conductive metal layer exposes part of the upper surface of the substrate; and etching of the bottom surface of the substrate forms a proximal opening to the inner passageway.

Methods of fabricating the nanoneedles on a surface of a substrate using a positive photoresist are provided. The methods include patterning a positive photoresist layer onto the hard photoresist layer and transferring the pattern from the positive photoresist layer to the hard photoresist layer. The methods can include exposing part of the upper surface of the substrate and form a patterned hard photoresist layer. In some aspects, the methods include depositing a magnetic material onto the part of the upper surface of the substrate and the patterned hard photoresist layer. In one or more aspects, the material on the conductive metal layer can be selected from the group consisting of iron, cobalt, nickel, gold, and oxides and alloys thereof. In some aspects, the material on the conductive metal layer can be a metal, including a transition metal such as iron, cobalt, nickel, or an oxide or alloy thereof. The etching of the patterned hard photoresist layer can form the nanoneedle having an inner passageway; and etching of the substrate can form a proximal opening to the inner passageway.

In any one or more aspects of the aforementioned embodiments, the nanoneedles can be magnetic nanoneedles, and the material deposited on the surface of the substrate can be a magnetic material. The magnetic material can be selected from the group consisting of iron, cobalt, nickel, and oxides and alloys thereof.

Methods of using the magnetic nanoneedle arrays are also provided. The methods can include applying an oscillating magnetic field to a magnetic nanoneedle to induce one or more of heating of the magnetic nanoneedle, vibration of the magnetic nanoneedle, and using them as a thermal probe. The methods can include penetrating the cell membrane with a magnetic nanoneedle. In some aspects, the methods include delivering an agent to a cell through the inner passageway connecting the proximal opening and the distal opening. In certain aspects, the methods include extracting an agent from a cell through the inner passageway connecting the proximal opening and the distal opening. The methods can also include measuring the inner temperature of cell organelles.

Other systems, methods, features, and advantages of the present disclosure of a nanoneedle array will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings like reference numerals designate corresponding parts throughout the several views.

DETAILED DESCRIPTION

Figure 1:
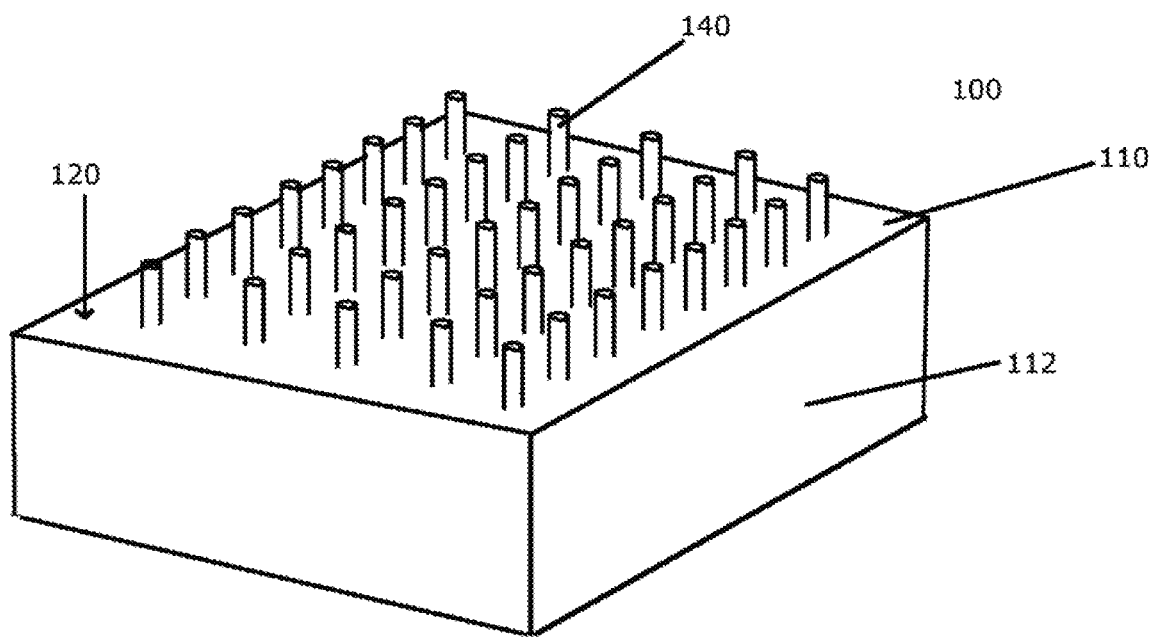
FIG. 1 is a perspective view of a magnetic nanoneedle array.

Described below are various embodiments of the present nanoneedle arrays, methods of making nanoneedle arrays, and methods of using nanoneedle arrays. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of micro-fabrication, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Nanoneedle Arrays

In various embodiments, the present disclosure provides nanoneedle arrays, arrays containing one or more needles having nanometer scale dimensions, methods of making nanoneedle arrays, and methods of using nanoneedle arrays.

The nanoneedle arrays can provide access to the cell cytoplasm with minimal cellular disruption. The nanoneedle arrays can be used to extract one or more agents from a cell and/or to administer one or more agents to a cell. Single nanoneedles or arrays of nanoneedles can be used as well to study the cell differentiation. In one or more aspects, the nanoneedles can be magnetic nanoneedles.

The nanoneedle array can be fabricated on a variety of substrates. The substrate can be a silicon substrate or a glass substrate. In preferred embodiments the substrate is a biocompatible substrate. The substrate can have a variety of dimensions, e.g. about 0.5 mm to 25 mm.

The substrate can be a silicon substrate. Silicon substrates can include substrates that are composed almost entirely of silicon (e.g., silicon wafers), silicon-on-insulator (SOI) substrates, silicon-on-sapphire substrate (SOS), SIMOX substrates, among others. Silicon (111) substrates can be used. Si(100) substrates may also be used. In some cases amorphous silicon substrates are used. In still other cases, substrates of sapphire, silicon carbide (SiC) and gallium arsenide (GaAs) can be used.

The substrate can be a glass substrate. Glass substrates can include borosilicate glasses, soda lime glasses, and aluminosilicate glasses. The substrate materials can be biocompatible and therefore don't affect cells or their inner parts. Highly doped silicon substrates can be used as a seed growing layer for the nanoneedle arrays. Arsenic or Phosphoros impurities doping the silicon to 1E18 levels can be used for achieving low resistivity values of 0.02 to 0.04 Ohm-cm.

The substrate can have an upper surface, wherein one or more nanoneedles can be grown at the upper surface, so that the nanoneedles can be attached to the upper surface. The nanoneedles can be perpendicular to the upper surface of the substrate, e.g. can form an angle with respect to the surface of about 80° to 100°, about 85° to 95°, about 87° to 93°, about 88° to 92°, about 89° to 91°, or about 90°.

The nanoneedle can have a hollow passageway extending along the length of the nanoneedle. The passageway can allow for the movement of agents through the nanoneedle, e.g. between a proximal opening in the nanoneedle (proximal to the substrate) and a distal opening in the nanoneedle (distal to the substrate). The passageway can have any internal diameter to accommodate a variety of agents. The passageway can have an internal diameter of about 50 nm to 1000 nm, about 50 nm to 800 nm, about 50 nm to 600 nm, about 100 nm to 500 nm, about 100 nm to 400 nm, or about 150 nm to 400 nm.

The nanoneedle can have a variety of dimensions to accommodate a variety of applications including differently sized cells and differently sized agents. The nanoneedle can have a width or outer diameter of about 100 nm to 1500 nm, about 100 nm to 1000 nm, about 200 nm to 1000 nm, about 250 nm to 1000 nm, or about 500 nm to 1000 nm. The nanoneedle can have a length of about 100 nm to 10000 nm, about 100 nm to 5000 nm, about 200 nm to 5000 nm, about 500 nm to 5000 nm, about 500 nm to 3000 nm, or about 500 nm to 2000 nm. The nanoneedle can have a large aspect ratio. In some embodiments the nanoneedle can have an aspect ratio of about 2 to 20, about 3 to 20, about 3 to 15, about 1 to 10, about 3 to 10, about 4 to 10, or about 5 to 10.

The nanoneedles can contain a non-magnetic material such as gold and oxides and alloys thereof. The nanoneedles can contain a magnetic material. Using a magnetic material can allow for the magnetic nanoneedle to respond to an applied magnetic field. In particular, the magnetic nanoneedle can vibrate and/or heat up in response to an oscillating magnetic field applied to the magnetic nanoneedle. The magnetic material can be iron, cobalt, nickel, oxides thereof, and alloys thereof. The magnetic material can include other magnetic and non-magnetic materials. The magnetic nanoneedles can contain different sections of different materials, for example, gold and iron to provide flexibility in terms of the specific application.

Figure 2:
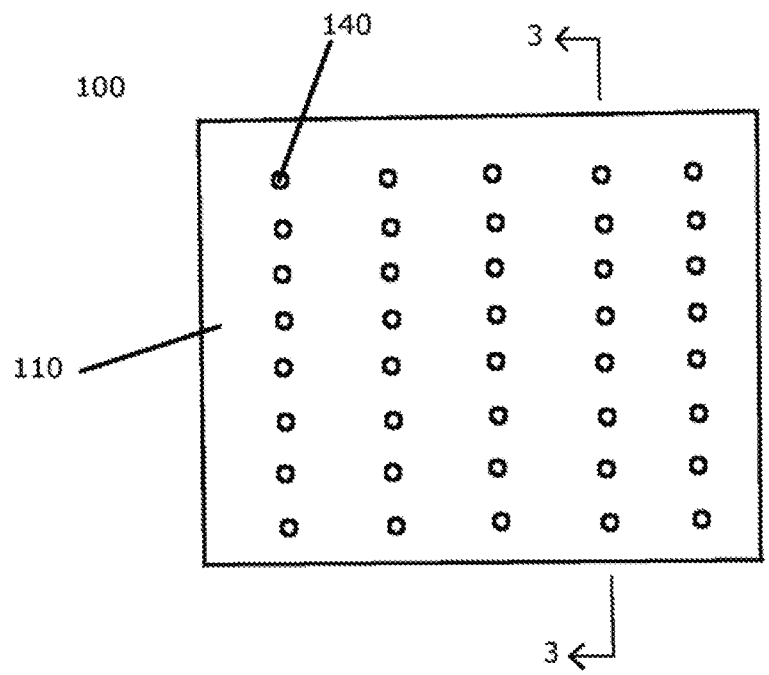
FIG. 2 is a top view of a magnetic nanoneedle array.
Figure 3:
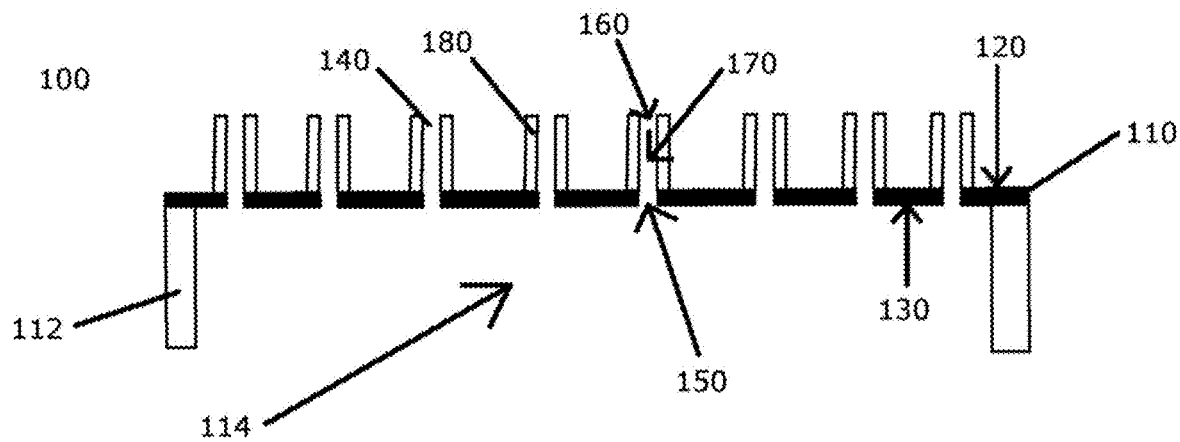
FIG. 3 is a sectional view along 3-3 of the magnetic nanoneedle array from FIG. 2.

FIGS. 1-3 of the present disclosure depict one embodiment of a magnetic nanoneedle array 100 on a substrate 110. The substrate has both an upper surface 120 and a lower surface 130. The nanoneedles 140 are attached to the upper surface 120 of the substrate 110. The nanoneedles 140 have both a proximal opening 150 and a distal opening 160 connected by a passageway 170 extending the length of the nanoneedle 140. The substrate can have side walls 112 forming an inner chamber 114 such as a microfluidic channel or chamber in fluid communication with the proximal opening 150.

Methods of Fabricating Nanoneedle Arrays

Methods of fabricating nanoneedle arrays on a substrate are provided. The fabrication methods can employ a variety of methods including deposition methods, patterning methods, electroplating methods, and etching methods. Examples of deposition methods include conventional chemical vapor deposition (CVD), low pressure chemical vapor deposition (LPCVD), atomic layer deposition (ALD), pulsed chemical vapor deposition (P-CVD), plasma enhanced atomic layer deposition (PE-ALD), electroplating, spin coating, sputtering, pulsed laser deposition, or combinations thereof. The methods can include depositing a metallic material onto the upper surface of the substrate and patterning the metallic material or depositing the metallic material onto a patterned sacrificial layer such as a photoresist to form the nanoneedle on the surface of the substrate.

The variety of lithography methods can include stereo lithography technics using structural resists. In variety of aspects, photolithography techniques are used preparing the substrate for electroplating. The methods may also include electron beam lithography or laser lithography.

Figure 4:
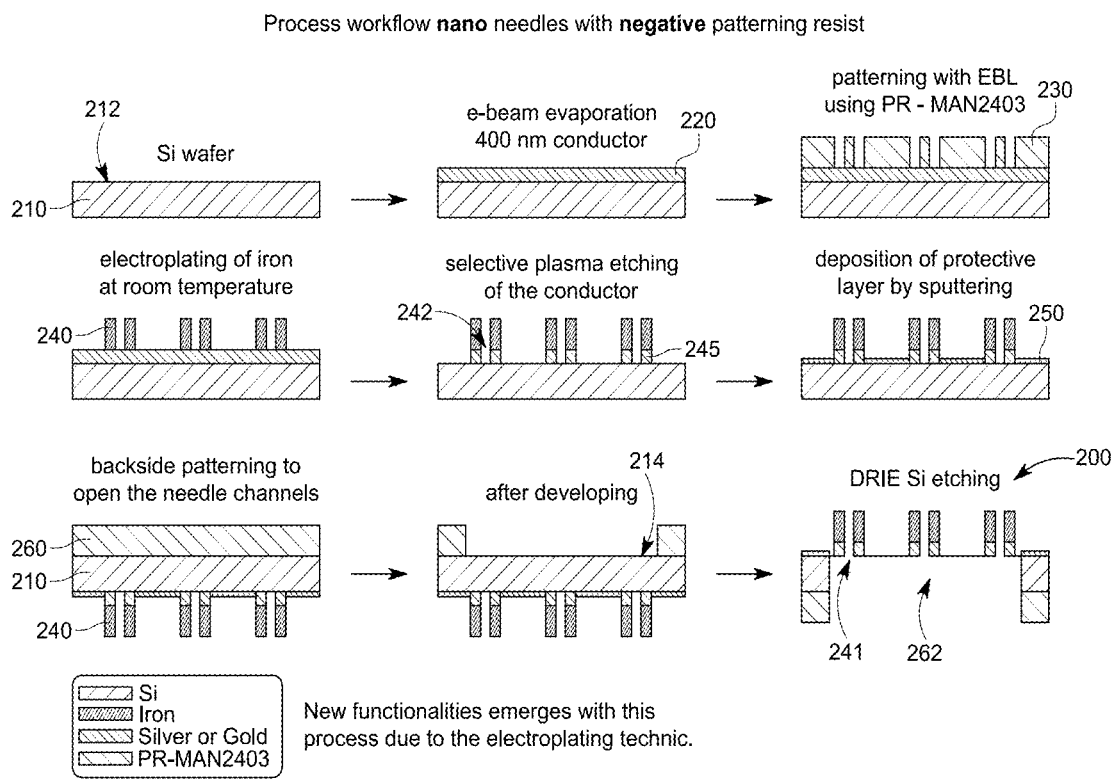
FIG. 4 is a workflow for one method of fabricating magnetic nanoneedle arrays using a negative patterning resist.
Figure 5:
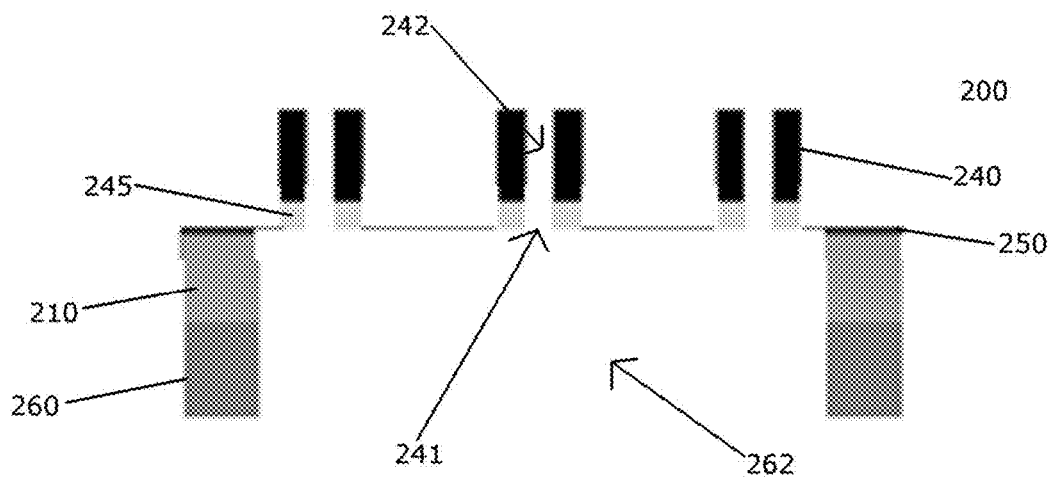
FIG. 5 is a sectional view of a magnetic nanoneedle array that can be fabricated using a negative patterning resist.

FIG. 4 depicts one embodiment of a method for fabricating a nanoneedle array 200 on a substrate 210 of the present disclosure. The nanoneedle array 200 is also depicted in FIG. 5. The method includes thin-film deposition of a conductive metal layer 220 onto an upper surface 212 of a substrate. The conductive metal layer can have a thickness of about 50 nm to about 500 nm, about 100 nm to 500 nm, or about 200 nm to 500 nm. In some embodiments the thin-film deposition can include electron beam (e-beam) evaporation. The methods include patterning a negative photoresist layer 230 onto the conductive metal layer 220. The patterning can include electron beam lithography. The negative photoresist layer can include SU-8, AZ 9260, or Ma-N 2403. The patterning can leave a part of the conductive metal layer exposed to form the nanoneedles. The method includes electroplating a magnetic material onto the conductive metal layer 220 using the patterned negative photoresist layer 230 to form the nanoneedle 240 having an inner passageway 242. Etching of the conductive metal layer 220 can leave a conductive metal portion 245 in the nanoneedle 240 while exposing a portion of the upper surface 212. The upper surface 212 can be protected when needed by depositing a thin protective layer 250. The protective layer can include Titalum or Chromium and in some aspect Gold or Silver. Etching of the bottom surface 214 of the substrate can form a proximal opening 241 to the inner passageway 242. The method can include patterning a second photoresist layer 260 onto the bottom surface 214 of the substrate prior to the etching of the bottom surface of the substrate. The etching of the bottom surface 214 of the substrate can form a channel from the patterned second photoresist layer.

Figure 6:
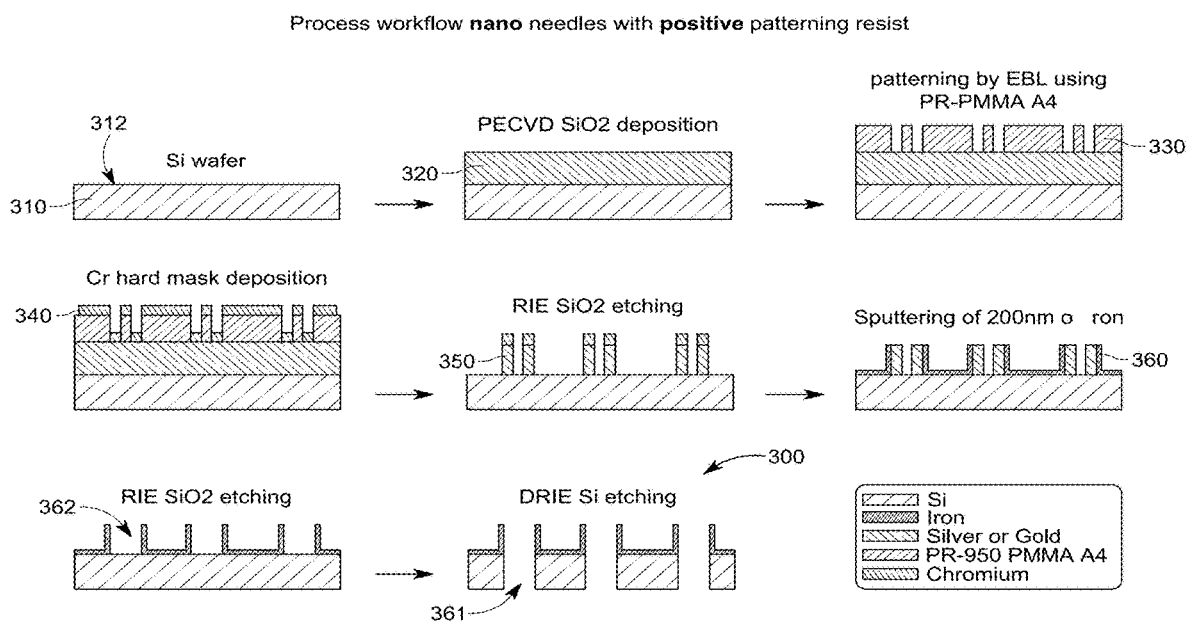
FIG. 6 is a workflow for one method of fabricating magnetic nanoneedle arrays using a positive patterning resist.
Figure 7:
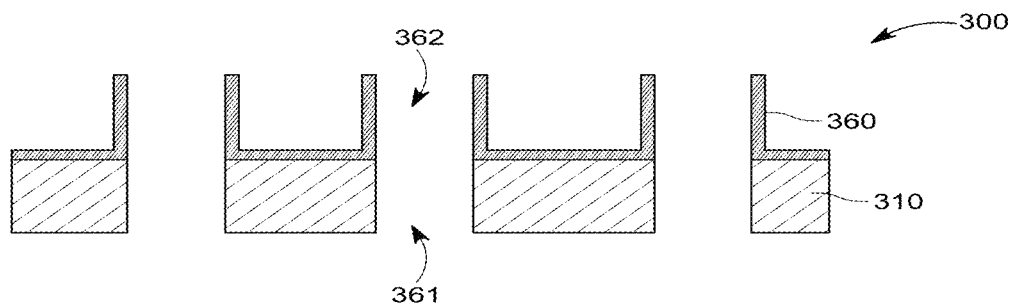
FIG. 7 is a sectional view of a magnetic nanoneedle array that can be fabricated using a positive patterning resist.

FIG. 6 depicts one embodiment of a method for fabricating a nanoneedle array 300 on a substrate 310. The nanoneedle array 300 is also depicted in FIG. 7. The method includes depositing a hard photoresist layer 320 onto an upper surface 312 of the substrate. The hard photoresist material can include a silicon oxide or silicon nitride or amorphous silicon layer grown on Gold. For example, the method can include plasma-enhanced chemical vapor deposition of a silicon oxide. The method include patterning a positive photoresist layer 330 onto the hard photoresist layer 320. The positive photoresist layer can include, for example, methacrylate polymers such as PMMA, S1800, or SPR-220. The positive photoresist layer 330 can be patterned, for instance, using electron beam lithography. The methods include transferring the pattern from the positive photoresist layer 330 to the hard photoresist layer 320 to form the pattered hard photoresist layer 350. The transfer can include exposure to DUV light, or deposition of a thin layer 340 of a hard photoresist material such as Cr followed by selective etching of the positive photoresist layer 330. The methods include depositing a material as described herein onto part of the upper surface 312 of the substrate 310 and the patterned hard photoresist layer 350. The methods include etching of the patterned hard photoresist layer 350 to form the nanoneedle 360 having an inner passageway 362. The methods can include etching of the substrate 310 to form a proximal opening 361 to the inner passageway 362.

Figure 8:
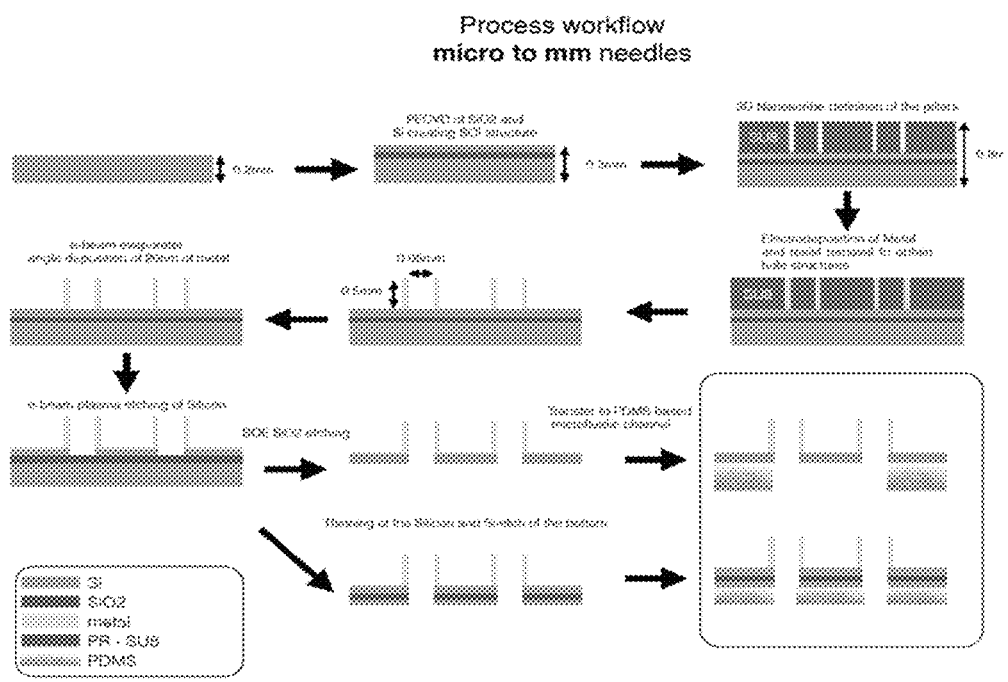
FIG. 8 is a workflow for fabricating magnetic needles of micro- to milli-meter dimensions.
Figure 9:
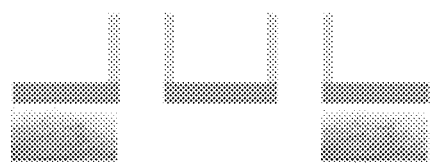
FIG. 9 is a sectional view of a magnetic needle having micro- to milli-meter dimensions.
Figure 10:
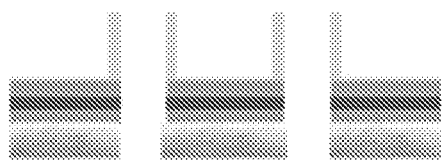
FIG. 10 is a sectional view of a magnetic needle having micro- to milli-meter dimensions.

FIG. 8 depicts an exemplary workflow for fabricating a metal nanoneedle array. Onto a silicon substrate a layer of silicon oxide and a layer of silicon can be deposited to create a silicon on insulator (SOI) structure. A photoresist can be patterned onto the SOI to form pillar structures. The metal can be electrodeposited onto the patterned photoresist, followed by removal of the photoresist to create the hole structures of the nanoneedles. Etching of the upper silicon layer can produce the nanoneedles on the silicon substrate. The methods can then include buffered oxide etching (BOE) of the silicon oxide to produce the nanoneedle array on the silicon substrate (FIG. 9) or thinning of the silicon oxide and etching the bottom silicon layer to produce the nanoneedles on a SOI substrate (FIG. 10).

Figure 11:
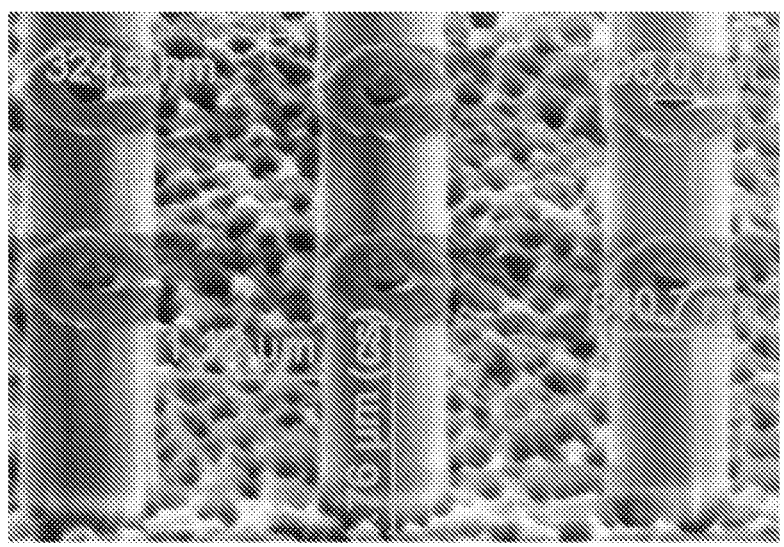
FIG. 11 is a scanning electron microscope (SEM) image of vertically-aligned silicon oxide magnetic nanoneedles on a silicium (Si<100>, 5 mOhm-cm) substrate depicting the dimensions of the nanoneedles.
Figure 12:
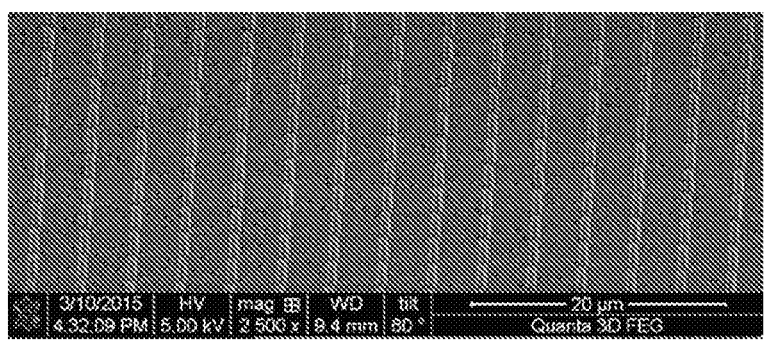
FIG. 12 is a scanning electron microscope (SEM) image of an array of vertically-aligned silicon oxide with chromium hard mask layer magnetic nanoneedles on a silicon substrate.

FIG. 11 and FIG. 12 are scanning electron microscope (SEM) images of nanoneedle arrays of the present disclosure. In these images a method with a positive resist has been used and the nanoneedles are made from the structural material of silicon oxide with a chromium cap.

Methods of Using Nanoneedle Arrays

While some delivery platforms rely on different approaches to exert forces on the cell membrane, such as a controlled centrifugal force (2). Others require cells to be in suspension (3) or a chemical modification of the substrate surface (4), thereby limiting their versatility.

Magnetic nanoneedles and nanoneedle arrays allow for two active mechanisms to locally disrupt the cell membrane:
 1. Vibration of the nanoneedle induced by the force exerted by a magnetic field on a magnetic material.
 2. Heating of the nanoneedle due to magnetization losses of a magnetic material in a magnetic field.

Figure 13:
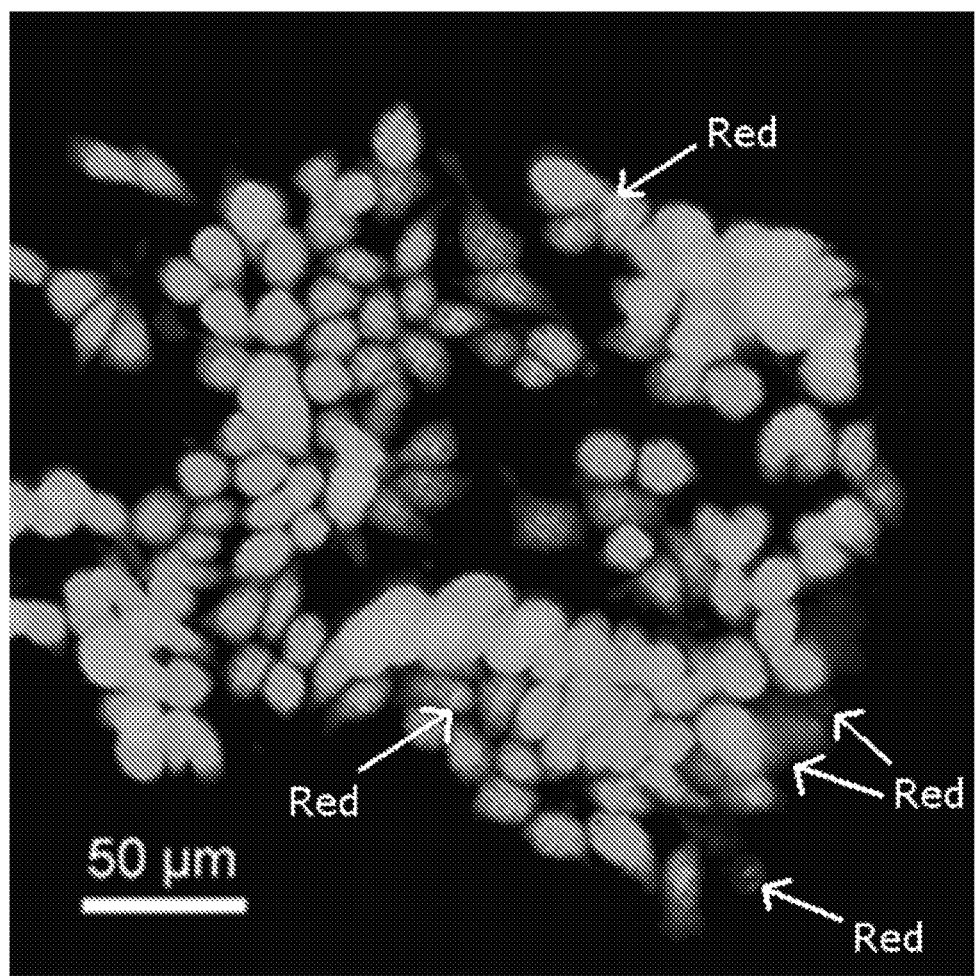
FIG. 13 is a fluorescence image depicting cell viability of HCT 116 cells cultured on a nanoneedle substrate. Viable cells were stained green, whereas dead cells were stained red.

Both of the mechanisms yield a local disruption of the cell membrane giving the nanoneedle access to the cytoplasm without affecting cell viability. To demonstrate the concept, the effect of the nanoneedles on cell viability was first observed. FIG. 13 shows a fluorescence microscopy image of a model cell line (HCT 116 colon cancer cells) growing on top of the nano needles. The Calcein AM/Ethidium homodimer-1 dye combination was used to assess cell viability, with the former dye emitting a green signal on live cells and the latter a red signal on dead cells. As observed, most of the cell population remains alive and viable after 24 hours of culture in the nanoneedle substrate.

Methods of using the magnetic nanoneedle arrays are provided. The methods can be used to nondestructively access the cytoplasm of a cell on the nanoneedle substrate. The methods can therefore be used to deliver one or more agents to the cell. The methods can also be used to extract an agent from the cell.

The methods can include applying an oscillating magnetic field to the magnetic nanoneedles. The oscillating magnetic field can induce heating of a magnetic nanoneedle. The oscillating magnetic field can include vibration of the magnetic nanoneedle. The heating and/or the vibration can cause a magnetic nanoneedle to penetrate the cell wall of a cell on the substrate.

The methods can include delivering an agent to a cell. Suitable agents to be delivered to the cell can include a therapeutic, prophylactic, or diagnostic agent. The agents to be delivered can include small molecules, proteins, or peptides. The agent to be delivered can be delivered through the inner passageway of the nanoneedle and into the cell.

It should be emphasized that the above-described embodiments are merely examples of possible implementations. Many variations and modifications may be made to the above-described embodiments without departing from the principles of the present disclosure. One skilled in the art will understand that many different materials can be used in the nanoneedle fabrication process. One skilled in the art will also understand that many different modes of operation of the nanoneedles are possible. All such modifications and variations are intended to be included herein within the scope of this disclosure and protected by the following claims.

REFERENCES (1) Berthing T, Bonde S, Rostgaard K R, Madsen M H, Sørensen C B, Nygºrd J, et al. Cell membrane conformation at vertical nanowire array interface revealed by fluorescence imaging. Nanotechnology 23:415102.
(2) Wang Y, Yang Y, Yan L, Kwok S Y, Li W, Wang Z, et al. 2014. Poking cells for efficient vector-free intracellular delivery. Nat. Commun. 5:4466. Available at http://www.ncbi.nlm.nih.gov/pubmed/25072981.
(3) Chen X, Zhu G, Yang Y, Wang B, Yan L, Zhang K Y, et al. 2013. A diamond nanoneedle array for potential high-throughput intracellular delivery. Adv. Healthc. Mater. 2:1103-1107.
(4) Shalek A K, Robinson J T, Karp E S, Lee J S, Ahn D-R, Yoon M-H, et al. 2010. Vertical silicon nanowires as a universal platform for delivering biomolecules into living cells. Proc. Natl. Acad. Sci. U.S.A 107:1870-1875.
(5) Chou L Y T, Ming K & Chan W C W. 2011. Strategies for the intracellular delivery of nanoparticles. Chem. Soc. Rev. 40:233-245.
(6) Takahashi K, Tanabe K, Ohnuki M, Narita M, Ichisaka T, Tomoda K, et al. 2007. Induction of Pluripotent Stem Cells from Adult Human Fibroblasts by Defined Factors. Cell 131:861-872.
(7) Yang Z, Deng L, Lan Y, Zhang X, Gao Z, Chu C-W, et al. 2014. Molecular extraction in single live cells by sneaking in and out magnetic nanomaterials. Proc. Natl. Acad. Sci. U.S.A. 111:10966-71

We claim:

1. A method of fabricating a nanoneedle array, the method comprising the steps of:
   depositing a thin-film of a conductive metal layer onto an upper surface of a substrate;
   patterning a negative photoresist layer onto the conductive metal layer;
   electroplating a material onto the conductive metal layer using the patterned negative photoresist layer to form the nanoneedle having an inner passageway;
   etching of the conductive metal layer to expose part of the upper surface of the substrate; and
   etching partially the bottom surface of the substrate to form a proximal opening to the inner passageway,
   wherein a first portion of the nanoneedle, proximal to the substrate, includes the conductive metal layer, and a second portion of the nanoneedle, distal from the substrate, includes the electroplated material.

2. The method of claim 1, further comprising patterning a second photoresist layer onto the bottom surface of the substrate prior to the etching of the bottom surface of the substrate; wherein the etching of the bottom surface of the substrate forms a channel from the patterned second photoresist layer.

3. The method of claim 1, further comprising:
   depositing a thin protective layer on the substrate, around the nanoneedle.

4. The method of claim 1, wherein the substrate comprises a silicon substrate or a glass substrate.

5. The method of claim 1, wherein the nanoneedle comprises a material selected from the group consisting of iron, cobalt, nickel, gold, and oxides and alloys thereof.

6. The method of claim 1, wherein the nanoneedle has a width of about 100 nm to 1000 nm.

7. The method of claim 1, wherein the nanoneedle has an aspect ratio of about 3 to 10.

8. The method of claim 1, wherein the nanoneedle array is a magnetic nanoneedle array.

* * * * *